United States Patent [19]
McCague et al.

[11] Patent Number: 5,898,075
[45] Date of Patent: Apr. 27, 1999

[54] PROCESS FOR THE SEPARATION OF THE ENANTIOMERS OF A BICYCLIC LACTAM

[75] Inventors: Raymond McCague, Cambridgeshire; Gerard Andrew Potter, Cambridge; Stephen John Clifford Taylor, Cambridgeshire; Brian Michael Adger, Cambridge, all of United Kingdom

[73] Assignee: Chirotech Technology Limited, Cambridge, United Kingdom

[21] Appl. No.: 08/776,602

[22] PCT Filed: Aug. 10, 1995

[86] PCT No.: PCT/GB95/01895

§ 371 Date: Mar. 13, 1997

§ 102(e) Date: Mar. 13, 1997

[87] PCT Pub. No.: WO96/06080

PCT Pub. Date: Feb. 29, 1996

[30] Foreign Application Priority Data

Aug. 19, 1994 [GB] United Kingdom .................... 9416857
Dec. 9, 1994 [GB] United Kingdom .................... 9425054

[51] Int. Cl.$^6$ .................................................. C07D 209/52
[52] U.S. Cl. ........................................... 548/452; 548/486
[58] Field of Search ...................... 548/452, 486

[56] References Cited

U.S. PATENT DOCUMENTS 5,102,890  4/1992  Bourzat et al. ..................... 514/299

FOREIGN PATENT DOCUMENTS 0 424 064  10/1990  European Pat. Off. .

OTHER PUBLICATIONS

Nakano et al., "A Facile Lipase–Catalyzed Resolution of 2–Azabicyclo[2.2.1]hept–5–en–3–ones", Tetrahedron: Asymmetry, vol. 5, No. 7, (1994), pp. 1155–1156.

Handa et al., "The Enantioselective Synthesis; of an Important Intermediate to the Antiviral, (–)–Carbovir", J. Chem. Soc. Perkin Trans., (1994), pp. 1885–1886.

Primary Examiner—Deborah C. Lambkin
Assistant Examiner—Jane C. Osowecki
Attorney, Agent, or Firm—Foley & Lardner

[57] ABSTRACT

A process is described for obtaining a single enantiomer from a racemic mixture of the bicyclic lactam 2-azabicyclo [2.2.1] hept-5-en-one by seeding a supersaturated solution of the lactam and a solvent with a single enantiomer of the lactam.

8 Claims, No Drawings

PROCESS FOR THE SEPARATION OF THE ENANTIOMERS OF A BICYCLIC LACTAM

This application is a 371 of PCT/GB95/01895 filed Aug. 10, 1995.

FIELD OF THE INVENTION

This invention relates to a process for the separation of the enantiomers of the bicyclic lactam 2-azabicyclo-[2.2.1]hept-5-en-3-one, and to the enhancement of an enantiomeric excess (ee) of one enantiomer in a mixture.

BACKGROUND OF THE INVENTION

2-Azabicyclo[2.2.1]hept-5-en-3-one is a useful intermediate for the manufacture of pharmaceutical entities. In particular, it can be used to prepare carbocyclic nucleosides which differ from the natural ribosyl nucleosides in having oxygen replaced by a methylene. Various carboxylic nucleosides have been demonstrated to possess useful therapeutic activity, for instance as antivirals and cardiac vasodilators. For the therapeutic purpose, it is preferred that the agents are obtained in single-enantiomer form, and this is conveniently accomplished by the use of the single enantiomers of the bicyclic lactam or derivatives thereof.

Various processes for obtaining the enantiomers of the bicyclic lactam are known. EP-A-0424064 discloses biocatalytic hydrolysis with enzymes that have a preference for one or other isomer, so that after the biotransformation of racemic lactam there are obtained one enantiomer as the untransformed lactam and the other enantiomer as ring-opened amino-acid. More recently, resolution of the bicyclic lactam through lipase-mediated resolution of the N-hydroxymethyl derivative has been reported by Nakano et al, Tetrahedron Asymmetry, 5: 1155–56 (1994).

SUMMARY OF THE INVENTION

The present invention is based on the discovery that, while procedures as described above offer effective means to obtain the single enantiomers of the bicyclic lactam, a simpler more economic procedure is available, since the enantiomers can be separated directly and efficiently by a direct crystallisation technique. We have found to our surprise that, in the case of the bicyclic lactam 2-azabicyclo [2.2.1]hept-5-en-3-one, the single enantiomer showed much lower solubility than the racemate in ethereal solvents. Direct enantiomer separation, without the need for resolving agents, has been achieved by seeding a supersaturated solution of the racemate with a single enantiomer, under controlled conditions. The separation may also be achieved for any derivative thereof which exhibits the same effect, e.g. carrying one or more substituents in the carbocyclic ring, or a N-substituent, e.g. N-acyl or another cleavable moiety.

Without wishing to be bound by theory, it seems that racemic lactam exists as a conglomerate of its enantiomers rather than the more common case where racemates crystallise in space groups containing both enantiomeric forms. Evidence for the presence of a conglomerate is that, when racemate is mixed with the single enantiomer in any proportion, at no point is the melting point depressed below that of the racemate (racemate m.p. 54° C.; enantiomer m.p. 98° C.). Further, differential calorimetric studies on the racemate showed a peak characteristic of a conglomerate.

Accordingly, a supersaturated solution of the lactam may be entrained by seeding with crystals of the single enantiomer to grow larger crystals having an excess of the isomer seeded, and leaving the opposite isomer enriched in the mother liquors. In order to make such an entrainment crystallisation procedure useful for the production of single-enantiomer lactam it is desirable that the optically-enriched lactam obtained can be raised in enantiomeric purity through recrystallisation. Nonetheless the overall procedure is a resolution leaving an issue of utilisation of the wrong enantiomer. If it could be racemized or the configuration inverted, then all material could in principle be directed to the required isomer.

According to a second aspect of the invention, it has been discovered that recrystallisation of optically-enriched lactam will give crystals of higher enantiomeric excess (ee). This means that methods that initially produce the lactam of low ee could become commercially useful. Such methods include entrainment of the racemate with seed crystals of the single enantiomer, as described above, or a method of asymmetric synthesis that produces material of unsatisfactory ee. Even a low initial ee of the lactam will provide, after a suitable number of crystallisations, some amount of a single isomer.

DESCRIPTION OF THE INVENTION

In the entrainment procedure, the conditions described below suffice in practice to achieve some separation of the enantiomers. Firstly, a saturated solution of the racemic lactam is prepared at a given temperature. Suitable solvents for the procedure include ethers such as t-butyl methyl ether (TBME) or di-isopropyl ether. Incorporation of a polar solvent additive such as i-propanol is also beneficial and allows more efficient enantiomer crystallisation.

An amount of racemic lactam is dissolved in the solvent by warming to effect complete dissolution. The solution is then cooled so that the solution becomes supersaturated and seeded with crystals of the single enantiomer. Once a certain amount of crystallisation has taken place, the crystals are harvested and show a greater weight excess of single enantiomer than is represented by the seed crystals. Also, the mother liquors now contain an excess of the enantiomer opposite to that used for the seeding. By recrystallisation of the crystals, single-enantiomer lactam (of high optical purity) can be obtained in greater amount than that of the seeds used in the initial crystallisation.

Mother liquors from the procedure containing an excess of one enantiomer can be resubjected to the above procedure but seeding with the opposite enantiomer. By an iterative process of crystallisation (cyclic entrainment), seeding with opposite enantiomers alternately, it is in principle possible to separate an amount of racemic lactam entirely into its enantomeric components.

Other techniques may be employed to achieve the same separation, such as, for instance, seeding the racemate solution with seeds of both enantiomers but which are of different particle sizes. Then, after crystallisation, the enantiomers may be separated by a size-separation process such as sieving.

In the enrichment procedure of this invention, for recrystallisation, a variety of solvents can be chosen and crystallisation induced by conventional techniques that obtain a supersaturated solution, such as by cooling of a saturated solution, by solvent evaporation from a saturated solution, or by addition of an additional solvent in which the lactam is less soluble. Suitable solvents for this purpose are, for example, methyl t-butyl ether, di-i-propyl ether or dichloromethane-heptane. Suitable solvent additives are, for example, alcohols such as ethanol, isopropanol or amides such as formamide or pyrrolidone; such additives allow enhanced enantiomer recovery, probably owing to their H-bonding properties.

The following Examples illustrate the applicability of the present invention.

EXAMPLE 1
Entrainment

Racemic 2-azabicyclo[2.2.1]hept-5-en-3-one (22 g) was dissolved in t-butyl methyl ether (200 ml) at 55° C. The solution was stirred and cooled to 20° C. and crystals of (−)-2-azabicyclo[2.2.1]hept-5-en-one added. After 1.5 h, the crystals (12 g) were harvested and shown by gas chromatographic analysis on a chiral column (Chrompak CP-cyclodextrin-B 236M19; 50 m) to be 14% ee in favour of the (−)-enantiomer. If there were no entrainment, an enantiomeric excess of 8.3% would be expected.

EXAMPLE 2
Enrichment

2-Azabicyclol[2.2.1]hept-5-en-3-one having 29% ee in favour of the (+)-enantiomer [132 g; an excess of 38 g (+)-isomer)] was recrystallised by addition of pentane to a dichloromethane solution to give 87 g crystals of 45% ee [an excess of 39 g (+)-enantiomer]. Further recrystallisation of this material gave 38 g crystals of 81% ee [an excess of 31 g (+)-enantiomer].

EXAMPLE 3
Enrichment

2-Azabicyclo[2.2.1]hept-5-en-3-one having 80% ee in favour of the (+)-enantiomer (2.27 kg) was stirred in dichloromethane (1.13 l) and heated to 70° C. until dissolution occurred. The solution was then cooled to 50° C. when crystallisation started. n-Hexane (2.26 l) was added over 30 min and the solution allowed to cool to ambient temperature. After filtration and drying the yield was 1.67 kg of the (+)-lactam having 88% ee. This material was recrystallised in the same way with 0.83 l dichloromethane and 1.67 l n-hexane, yielding 1.37 kg of (+)-lactam having 95% ee. A final crystallisation from 0.68 l dichloromethane and 1.37 l n-hexane yielded 1.15 kg (+)-lactam having 99.2% ee.

EXAMPLE 4
Cyclic Entrainment

A solution of racemic γ-lactam (1 kg) at a concentration of 16.83 g %, having a 2% ee in favour of the (−) enantiomer was prepared in a solvent composed of 10% w/w isopropanol in di-i-propyl ether. The solution was warmed to 45° C. to effect complete dissolution, filtered, then cooled to 20° C. The solution was stirred rapidly by means of an overhead mechanical stirrer, and 50 mg of (−) enantiomer seed crystals added. After 1 hour at 20° C. the crystalline product was collected by filtration. This typically produced 5–7 g of 85–90% ee (−) enantiomer.

To the filtrate was added an equal mass of racemate to the mass of product removed by crystallisation (i.e. 5–7 g). The solution was warmed again to 45° C. to ensure complete dissolution, then cooled to 20° C. The solution was stirred rapidly and 50 mg of (+) enantiomer seed crystals added. After 1 hour the crystals were collected by filtration to typically give 5–7 g of 85–90% ee (+) enantiomer.

This process was repeated over a total of 10 alternating cycles, 5 seeding with (−) and 5 seeding with (+). The products from the crystallisations of the individual enantiomers were combined to give 31.91 g of 86% ee (−) enantiomer and 31.06 g of 86% ee (+) enantiomer. Recrystallisation afforded 25 g of each pure enantiomer (100% ee). Thus by this process a total of 0.25 g of (−) enantiomer seeds yielded 25 g of single enantiomer (−) lactam.

A summary of the entrainment carried out in this way is tabulated below.

| Cycle No. | C/g (%) | Mass of Crystals (g) | ee (%) |
|---|---|---|---|
| 1(−) Start | 16.83 | | |
| Finish | 16.25 | 7.64 | 86 (−) |
| 2(+) | 16.83 | | |
| | 16.32 | 6.03 | 87 (+) |
| 3(−) | 16.69 | | |
| | 16.18 | 5.06 | 90 (−) |
| 4(+) | 16.83 | | |
| | 16.32 | 6.50 | 85 (+) |
| 5(−) | 17.05 | | |
| | 16.61 | 6.81 | 84 (−) |
| 6(+) | 16.98 | | |
| | 16.54 | 6.63 | 85 (+) |
| 7(−) | 17.05 | | |
| | 16.61 | 6.12 | 85 (−) |
| 8(+) | 17.05 | | |
| | 16.61 | 5.58 | 84 (+) |
| 9(−) | 17.05 | | |
| | 16.61 | 6.28 | 87 (−) |
| 10(+) | 17.05 | | |
| | 16.61 | 6.32 | 87 (+) |
| Total (−) | Total | 31.91 | 86 (−) |
| | Recrystallised | 25.6 | 100 (−) |
| Total (+) | Total | 31.06 | 86 (+) |
| | Recrystallised | 24.8 | 100 (+) |

We claim:

1. A process for obtaining an enantiomer of the bicyclic lactam 2-azabicyclo[2.2.1]hept-5-en-3-one, which comprises seeding a supersaturated solution comprising a solvent and the racemate of the lactam with a single enantiomer of the lactam.

2. A process for increasing the enantiomeric excess of one of a mixture of enantiomers of the lactam 2-azabicyclo[2.2.1]hept-5-en-3-one, which comprises recrystallisation of crystals of the lactam.

3. A process according to claim 1 wherein the solvent is an ether.

4. A process according to claim 1, wherein the solution comprises a solvent additive.

5. A process according to claim 4, wherein the solvent additive is an alcohol or amide.

6. A process according to claim 2, which comprises the prior asymmetric synthesis of the lactam.

7. A process according to claim 2, further comprising entraining the racemic lactam with seeds of a single enantiomer of the lactam by crystallization.

8. A process according to claim 2, which comprises seeding a solution of the racemate of the lactam alternately with opposite single enantiomers of the lactam and, between seedings, crystallising out and collecting an enantiomer of the lactam.

* * * * *